US00PP35795P2

(12) United States Plant Patent
Trees

(10) Patent No.: US PP35,795 P2
(45) Date of Patent: May 7, 2024

(54) ***BUDDLEJA* PLANT NAMED 'SFF21-026'**

(50) Latin Name: ***Buddleja* x *hybrida***
Varietal Denomination: SFF21-026

(71) Applicant: Sunrise Farm Flowers, LLC, Arroyo Grande, CA (US)

(72) Inventor: Scott C. Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

(21) Appl. No.: 18/186,179

(22) Filed: Mar. 19, 2023

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ..... A01H 5/02; A01H 5/00; A01H 6/00
See application file for complete search history.

(56) References Cited

U.S. PATENT DOCUMENTS

PP24,016 P3 * 11/2013 Werner ..... Plt./242
PP26,547 P3 * 3/2016 Werner ..... A01H 6/00 Plt./242
PP33,843 P2 * 1/2022 Trees ..... Plt./242

* cited by examiner

*Primary Examiner* — June Hwu
(74) *Attorney, Agent, or Firm* — Weatherly IP Solutions, LLC; James M. Weatherly

(57) ABSTRACT

A new cultivar of *Buddleja* named 'SFF21-026' that is distinguishable by its prostate growth habit whose stems arch downwards when laden with flowers (inflorescences). The inflorescences of 'SFF21-026' are slender conical in shape and bear approximately 300 outward-facing flowers. The flowers of 'SFF21-026' are rose-pink in color and exhibit dark orange eyes and remain in bloom continually from May to September. 'SFF21-026' grows and flowers very rapidly. In combination, these characteristics distinguish 'SFF21-026' from all other varieties of *Buddleja* known to the inventor.

2 Drawing Sheets

Genus and species: *Buddleja* x *hybrida*.
Variety denomination: 'SFF21-026'.

BACKGROUND

The present disclosure relates to a new and distinct cultivar of *Buddleja* plant, also known as butterfly bush, a perennial or shrub that is grown for use as an ornamental landscape and container plant and as a hanging basket. The new variety is known botanically as *Buddleja* x *hybrida* and will be referred to hereinafter by the cultivar name 'SFF21-026'.

'SFF21-026' originates from a *Buddleja* breeding program, which was started in 2018 and conducted at the inventor's nursery in Arroyo Grande, California. The aim of the breeding program is to develop a series of compact varieties of *Buddleja* x *hybrida* with pendulous habits suitable for use in hanging baskets and planted containers, bearing flowers in a range of colors.

The breeding of 'SFF21-026' commenced in fall 2018 with the harvesting of open pollinated seeds from *Buddleja* 'Lavender Cascade' (U.S. Plant Pat. No. 30,635) which is the female parent variety. The male parent is unknown. The harvested seeds were sown and grown out and evaluated for plant habits in three growing cycles from 2019 to 2021 when the inventor chose 'SFF21-026' for commercial introduction.

'SFF21-026' was first asexually propagated by the inventor in Spring 2021 in a greenhouse at the inventor's nursery in Arroyo Grande, California using stem cuttings. The inventor has confirmed that 'SFF21-026' is stable and reproduces true to type in successive generations of asexual reproduction.

SUMMARY

The following traits have been repeatedly observed and represent the distinguishing characteristics of 'SFF21-026'. 'SFF21-026' has not been tested under all possible conditions and phenotypic differences may be observed with variations in environmental, climatic, and cultural conditions, without however, any variance in genotype.

1. 'SFF21-026' exhibits a pendulous growth habit.
2. The stems of 'SFF21-026' arch downwards when laden with flowers (inflorescences).
3. The inflorescences of 'SFF21-026' are slender conical in shape and bear approximately 300 outward-facing flowers.
4. The flowers of 'SFF21-026' are rose-pink in color and exhibit dark orange eyes due to that coloration within the central corolla tube.
5. 'SFF21-026' remains in bloom continually from May to September.
6. 'SFF21-026' grows and flowers rapidly. Full and flowering plants may be produced in 1 or 2-gallon containers in 10 to 12 weeks from planting a well-rooted cutting or young plant.

DESCRIPTION OF THE PHOTOGRAPHS

The accompanying color photographs illustrate the overall appearance of the new *Buddleja* cultivar 'SFF21-026' showing the colors as true as it is reasonably possible to obtain in colored reproductions of this type. Photographs were taken in August 2022 in Santa Barbara, California from a one-year-old plant grown outdoors in a 2-gallon container, with one pinch after initial cutting establishment and without any chemical growth regulators. Colors in the photographs may differ from the color values cited in the detailed botanical description, which more accurately describes the actual colors of the new variety 'SFF21-026'.

DESCRIPTION OF THE NEW VARIETY

Figure 1:
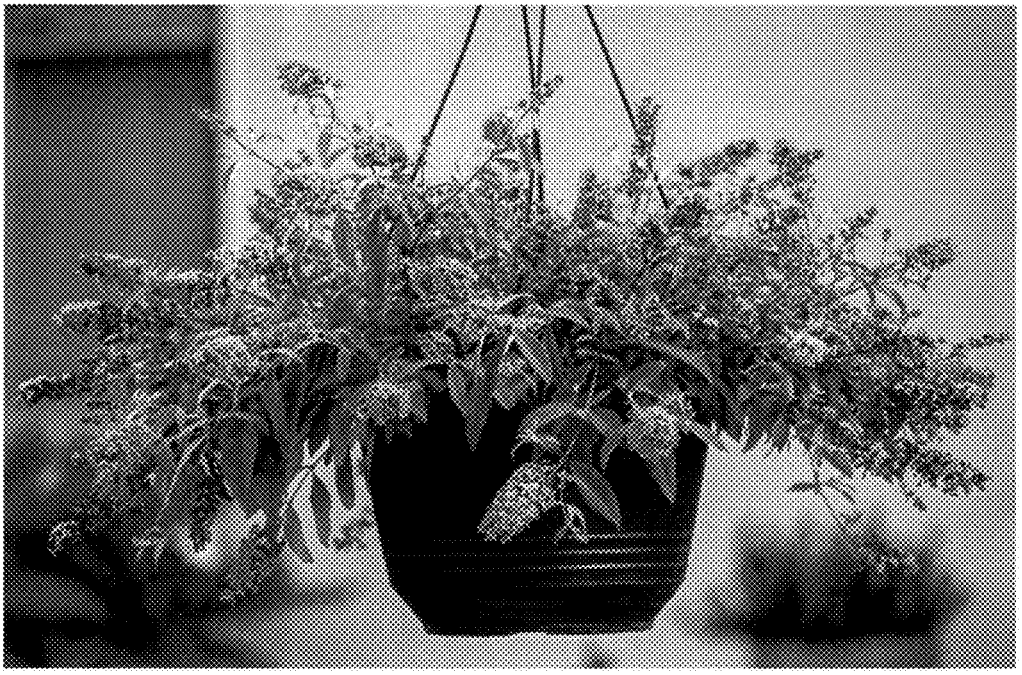
FIG. 1 depicts an entire plant in flower of 'SFF21-026' and shows its use as a hanging basket plant.
Figure 2:
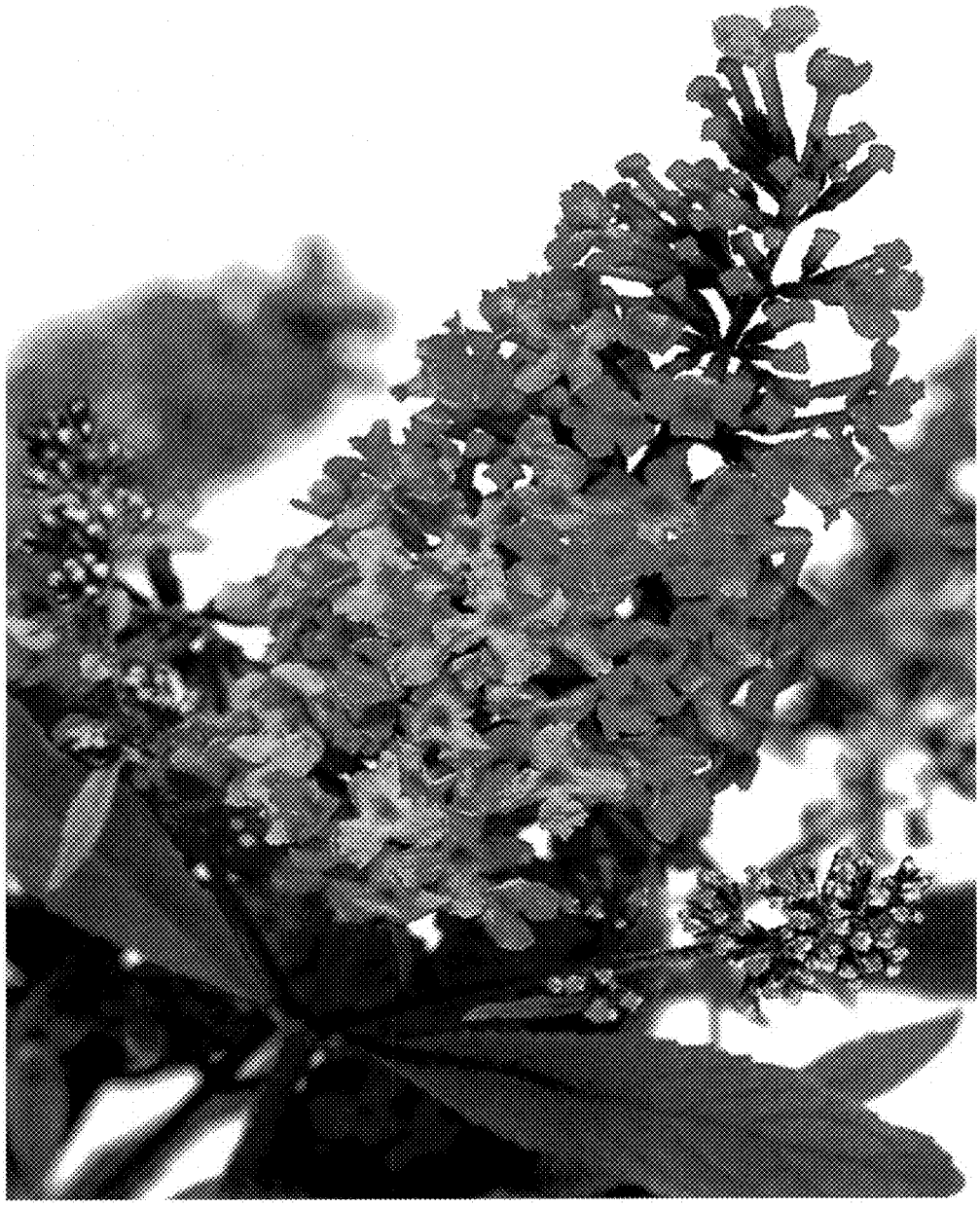
FIG. 2 depicts a close-up view of the inflorescences of 'SFF21-026' showing the panicles of rose-pink flowers with dark orange eyes.

The following detailed descriptions set forth the distinctive characteristics of 'SFF21-026'. Observations, measurements, values, and comparisons were collected in August 2022 in Santa Barbara, California from a one year old plant which had been growing outdoors in full sun in a 2-gallon container, with one pinch after initial cutting establishment and without any chemical growth regulators. Color determinations were made in accordance with The 2007 Royal Horticultural Society Colour Chart from London England, except where general color terms of ordinary dictionary significance are used.

Plant:

*Commercial classification.*—Shrub and perennial.

*Common name.*—Butterfly bush.

*Type.*—Ornamental.

*Uses.*—Hanging baskets, container plant for the deck or patio, perennial plant in an herbaceous border or shrub planting in the landscape. Stems and foliage may be used in cut flower arrangements.

*Container size.*—Suggested size is 1-gallon or 2-gallon container, or 8-inch-10-inch hanging basket.

*Cultural requirements.*—Well-drained soil, full sun, and moderate water.

*Blooming seasons.*—Continually in bloom from May to September.

*Vigor.*—Rapid growth rate. Plant will fill out a 1-gallon contain in 12-14 weeks from planting a rooted cutting.

*Plant habit.*—Prostrate, flowering stems arching downwards.

*Dimensions.*—30 cm in height, 90 cm in width.

*Hardiness.*—Hardy to USDA Hardiness Zone 5.

*Heat and humidity tolerance.*—Good, performs well in hot humid conditions.

*Drought tolerance.*—High.

*Pest and disease susceptibility.*—None.

Botanical classification: *Buddleja* x *hybrida* 'SFF21-026'.

*Genus.*—*Buddleja.*

*Species.*—x *hybrida.*

*Denomination.*—'SFF21-026'.

Parentage: 'SFF21-026' is a hybrid that resulted from the cross-pollination of the following parent plants:

*Female parent.*—*Buddleja* 'Lavender Cascade' (U.S. Plant Pat. No. 30,635).

*Male parent.*—Unknown variety.

Propagation:

*Propagation.*—Softwood cuttings taken above or below the node.

*Root system.*—Fibrous.

*Time to initiate rooting.*—2-3 weeks are required to produce a cutting which is viable on its own roots.

*Temperature to initiate rooting.*—Under greenhouse conditions, 20° Centigrade.

*Crop time.*—From planting and pinching (stopping) a well-rooted cutting or young plant, 10-12 weeks are needed to produce a full and flowering 1-gallon or 2-gallon container.

*Special growing requirements.*—For a long-term landscape planting, prune stems back to 3 inches-4 inches in length in early spring of each year.

Stem, branches:

*Description.*—Plant is strongly apically dominant, sending up basal stems after initial pinch or stop after planting. These basal stems grow rapidly and bear terminal paniculate inflorescences. Secondary stems begin to develop as the basal stems begin to flower. Secondary stems are relatively short and only begin to flower once the inflorescences on the basal stems have finished.

*Basal stems.*—Shape: Square with rounded edges. Length: 30 cm-35 cm from base to base of inflorescence, 50 cm-55 cm in length including the inflorescence. Diameter: 5 mm at stem base, 4 mm immediately below inflorescence. Stem surface: Puberulent, appears downy, color 196D. Stem color: N144D with saturated anthocyanin pigmentation on solar-facing surfaces, anthocyanin color 185A. Internode distance: Varies between 5 cm and 6.5 cm. Stem strength: Moderately stiff and wiry.

*Secondary stems.*—Quantity: 3-4 pairs at each basal stem node. Description: As basal stems except dimensions, length up to 10 cm, diameter up to 2 mm, and internode distance 2.5 cm to 3.5 cm.

Foliage:

*Type.*—Evergreen.

*Leaf arrangement.*—Opposite.

*Leaf division.*—Simple.

*Leaf quantity.*—8-10 leaves per basal stem, 2-6 leaves per secondary stem.

*Leaf shape.*—Lanceolate.

*Leaf base.*—Attenuate.

*Leaf apex.*—Acute.

*Leaf dimensions.*—Up to 8.5 cm in length, 3.5 cm in width.

*Leaf color* (*adaxial surface*).—144A.

*Leaf color* (*abaxial surface*).—138C.

*Leaf surface* (*both*).—Lightly puberulent.

*Leaf margins.*—Serrate, teeth irregularly spaces, approximately 3 teeth per cm., tooth depth 1.5 mm.

*Leaf venation.*—Pinnate, slightly depressed on adaxial surface, raised on abaxial surface.

*Vein color* (*adaxial surface*).—144A (as leaf).

*Vein color* (*abaxial surfaces*).—138C (as leaf, except midrib lighter, 139D.

*Leaf attachment.*—Sessile.

Peduncle:

*Dimensions.*—7 mm in length, 1 mm in diameter.

*Shape.*—Terete.

*Surface.*—Lightly puberulent.

*Color.*—187B.

Inflorescence:

*Inflorescence*.—Terminal cymose panicle.

*Dimensions*.—15 cm-20 cm in length, 4.5 cm-5.0 cm in width at base.

*Shape*.—Slender elongated cone.

*Lastingness*.—Whole inflorescence bears fresh flowers for 5-7 days before flowers senesce from base to apex. Some color remains in each inflorescence for 3-4 weeks.

*Fragrance*.—Pleasantly fragrant, lilac-like.

Pedicel:

*Description*.—Each short pedicel subtends one pair of flowers.

*Dimensions*.—2 mm in length and 0.5 mm in diameter.

*Pedicel shape*.—Terete.

*Pedicel color*.—187B.

*Pedicel surface*.—Lightly puberulent.

Bud:

*Shape*.—Cylindrical with hemispherical capitate apex.

*Dimensions*.—5 mm in length, 3 mm in diameter except capitate apex 2 mm in diameter.

*Color*.—63B except capitate apex darker, 61A.

*Surface*.—Smooth, glabrous, matte.

Flowers:

*Shape*.—Salverform, consisting of slender corolla tube (fused petal bases) and rotate free terminal petal lobes.

*Description*.—Flowers densely arranged in the inflorescence with outward-facing petal lobes rose-pink in color and corolla tube inner surface dark orange in color, appearing as a central eye.

*Quantity*.—From 5 to 7 flowers per cyme, approximately 50 cymes per inflorescence. Overall, approximately 300 flowers per inflorescence.

*Dimensions*.—9 mm in length, 8 mm in diameter (across petal lobe apices).

*Corolla*.—Dimensions: 7 mm in length, 2 mm in diameter. Surfaces (both): Glabrous and glossy. Color (inner and outer): 169B.

*Petals* (*free petal lobes*).—Dimensions: 2.5 mm in length, 2 mm in width. Surfaces (both): Glabrous. Color (adaxial and abaxial surfaces): 73A.

Calyx, sepals:

*Calyx dimensions*.—3 mm in length, 2 mm in diameter.

*Calyx shape*.—Narrow campanulate, 3-4 sepals fused at base.

*Sepals*.—Quantity: 4. Shape: Lanceolate. Dimensions: 1.0 mm-1.5 mm. in width. Apex: Acute. Margin: Entire. Surface: Glabrous. Color (both surfaces): 178B.

Reproductive organs:

*Description*.—Reproductive organs tiny and difficult to observe closely even with aid of magnifying glass.

*Stamens*.—Quantity, arrangement: 4, fused into wall of corolla tube. Filaments: Very short and positioned towards base of corolla tube, less than 1 mm in length, fine and white in color. Anthers: Tiny, narrow, less than 1 mm in length, white. Pollen: None observed.

*Pistil*.—Quantity: 1, style less than 1 mm in length, white. Stigma: Not observed.

*Ovary*.—Not observed.

*Seed*.—No seed has been observed.

COMPARISON WITH PARENTS AND CLOSEST KNOWN VARIETY

'SFF21-026' may be compared with the female parent variety, 'Lavender Cascade' as follows: Although both varieties 'SFF21-026' and 'Lavender Cascade' exhibit a prostrate plant habit, the habit of 'SFF21-026' is markedly more pendulous. Whereas as the flowers of 'SFF21-026' are rose-pink in color, the flowers of 'Lavender Cascade' are fertile and lavender in color. In addition, the leaves of 'SFF21-026' are shorter in length (up to 8.5 cm in length) when compared with the leaves of 'Lavender Cascade' which are up to 13 cm in length.

The male parent variety of 'SFF21-026' is unknown: no comparison is possible.

'Lavender Cascade' is the closest variety of *Buddleja* known to the inventor.

I claim:

1. A new and distinct cultivar of *Buddleja* Plant Named 'SFF21-026' as described and illustrated herein.

* * * * *